(12) United States Patent
Rastrelli et al.

(10) Patent No.: US 8,540,972 B2
(45) Date of Patent: Sep. 24, 2013

(54) SUNSCREEN PRODUCT COMPRISING HYDROXYAPATITE AS PHYSICAL FILTER

(75) Inventors: Gianbattista Rastrelli, Manerba Del Garda (IT); Luigi Rigano, Milan (IT); Giancarlo Gazzaniga, Savice Terme (IT)

(73) Assignee: Kalichem Italia S.R.L., Brescia (IT)

( * ) Notice: Subject to any disclaimer, the term of this patent is extended or adjusted under 35 U.S.C. 154(b) by 0 days.

(21) Appl. No.: 13/138,687

(22) PCT Filed: Mar. 22, 2010

(86) PCT No.: PCT/IB2010/051226
§ 371 (c)(1),
(2), (4) Date: Sep. 19, 2011

(87) PCT Pub. No.: WO2010/109400
PCT Pub. Date: Sep. 30, 2010

(65) Prior Publication Data
US 2012/0014891 A1    Jan. 19, 2012

(30) Foreign Application Priority Data
Mar. 23, 2009 (IT) .............................. MI2009A0448

(51) Int. Cl.
*A61K 8/04* (2006.01)
*A61K 8/06* (2006.01)
*A61Q 17/04* (2006.01)

(52) U.S. Cl.
USPC .......................................................... 424/60

(58) Field of Classification Search
None
See application file for complete search history.

(56) References Cited

U.S. PATENT DOCUMENTS

| 6,730,309 B2 | 5/2004 | Horino |
| 2002/0086039 A1 | 7/2002 | Lee et al. |
| 2005/0129640 A1* | 6/2005 | Laurent .......................... 424/63 |
| 2008/0160088 A1 | 7/2008 | Mackowiak |

FOREIGN PATENT DOCUMENTS

| EP | 1 837 013 | 9/2007 |
| FR | 2 812 194 | 2/2002 |
| JP | 03-200721 | 9/1991 |
| JP | 05-025458 | 2/1993 |
| JP | 05-032518 | 2/1993 |
| JP | 06-321748 | 11/1994 |
| JP | 07-031864 | 2/1995 |
| JP | 2005-298475 | 10/2005 |
| JP | 2006-241012 | 9/2006 |
| WO | WO 96/41611 | 12/1996 |
| WO | WO 2007/051547 | 5/2007 |

OTHER PUBLICATIONS

Holzmann et al, "hydroxyapatite Particles as Novel Low-Refractive Index Additives for the Long Term UV Protection of Transparanet Composite Materials", J. Mater. Chem. 2009, 19, 8102-8106.*

(Continued)

*Primary Examiner* — Carlos Azpuru
(74) *Attorney, Agent, or Firm* — Collard & Roe, P.C.

(57) ABSTRACT

The present invention concerns the use of hydroxyapatite as the physical sunscreening agent in synergistic association with at least one chemical sunscreening agent, in products designed for application to the skin in order to protect the same from solar UV radiation. Particularly, cosmetic compositions are described comprising the sunscreen product having screening capability, high dermal tolerance and a low whitening effect on the skin.

18 Claims, 1 Drawing Sheet

(56) References Cited

OTHER PUBLICATIONS

COLIPA International Sun Protection Factor (SPF) Test Method, Document 001-2003, Feb. 2003, Japan Cosmetic Industry Association (JCIA), pp. 1-51.
Ashikaga T. et al. "Effect of the photocatalytic activity of $TiO_2$ on plasmid DNA," *Mutation Res.* 466, (2000), pp. 1-7.
Fairhurst, D. "Surface Coating and the Optimization of Microfine Oxides in Sunscreen Formulations. A new technology for sunscreen development," *Cosmet Toil*, vol. 112, Oct. 1997, pp. 81-84 and 86-88.
Kobayashi, M. et al. "Photocatalytic Activity of Titanium Dioxide and Zinc Oxide. The effect of organic and inorganic surface treatments," *Cosmet Toil*, vol. 112, Jun. 1997, pp. 83-86.
Tan, M.-H. et al. "A pilot study on the percutaneous absorption of microfine titanium dioxide from sunscreens," *Australas J Dermatol*, 37, (1996), pp. 185-187.
Cai, R. et al. "Photokilling of Malignant Cells with Ultrafine $TiO_2$ Powder," 1991, *Bull Chem Soc Jpn*, 64, pp. 1268-1273.
Lademann J. et al. "Penetration of Titanium Dioxide Microparticles in a Sunscreen Formulation into the Horny Layer and the Follicular Orifice," 1999, *Skin Pharmacol Appl Skin Physiol*, 12, pp. 247-256.
Warner W. G. et al. "Oxidative damage to nucleic acids photosensitized by titanium oxide," 1997, Free Radic Biol Med, 23, pp. 851-858.
International Search Report of PCT/IB2010/051226, Feb. 2, 2011.
Written Opinion of the International Searching Authority of PCT/IB2010/051226, Feb. 2, 2011.

\* cited by examiner

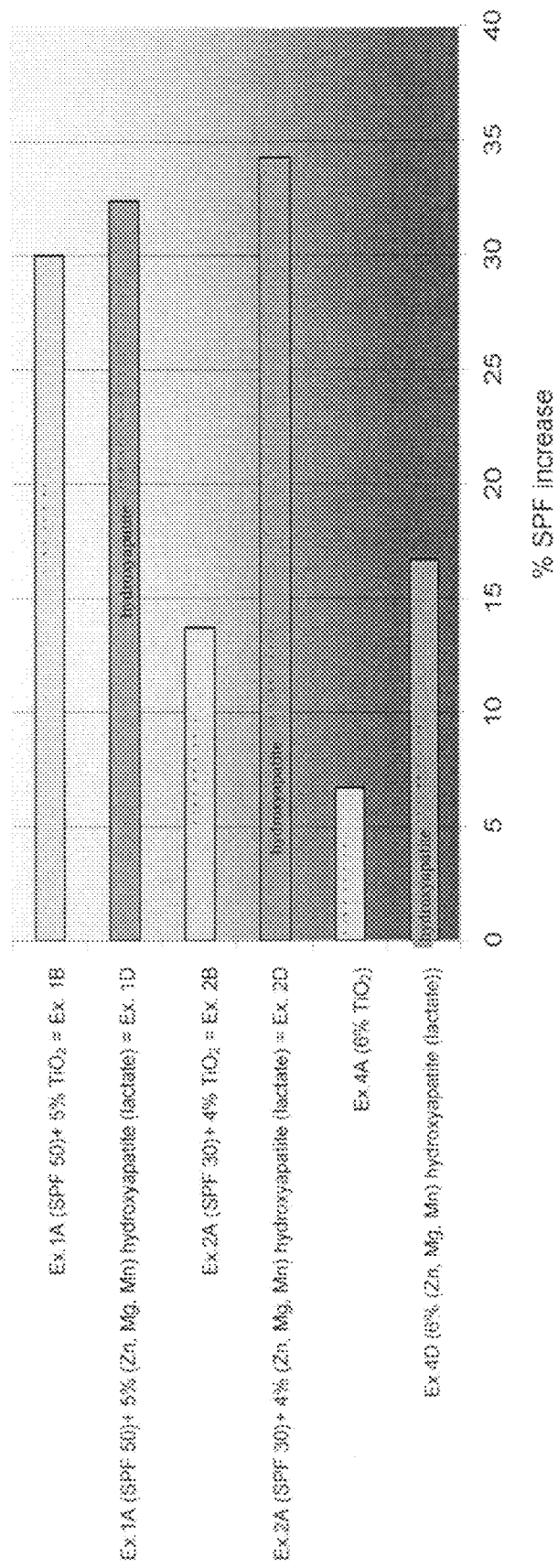

SUNSCREEN PRODUCT COMPRISING HYDROXYAPATITE AS PHYSICAL FILTER

CROSS REFERENCE TO RELATED APPLICATIONS

This application is the National Stage of PCT/IB2010/051226 filed on Mar. 22, 2010, which claims priority under 35 U.S.C. §119 of Italian Application No. MI2009A000448 filed on Mar. 23, 2009, the disclosure of which is incorporated by reference. The international application under PCT article 21(2) was published in English.

FIELD OF THE INVENTION

The present invention concerns the use of hydroxyapatite as physical sunscreening agent in products designed for application to the skin in order to protect the same from solar UV radiation. Particularly, cosmetic compositions are described comprising hydroxyapatite as physical sunscreening agent having screening capability, high dermal tolerance and a lower whitening effect than other physical sunscreening agents.

STATE OF THE ART

Prolonged exposure to ultraviolet (UV) rays, whether intermittent or chronic, particularly in the middle hours of the day and without suitably preparing the skin or without a rest period to promote skin cell regeneration, is a factor that can is cause various skin affections such as erythema, pimples, blisters, hyperpigmentation, elastosis, epidermal rupture, photoageing and photo-carcinogenesis. However, if on the one hand it is known that excessive exposure can be harmful and dangerous, on the other hand it is also known that intelligent and conscious exposure has undoubted beneficial effects, particularly in children and the elderly, as it stimulates vitamin D synthesis in the body which assists ossification. Hence it is a case of supporting more informed and balanced attitudes, such that the sun's benefits are enjoyed while limiting photo-induced damage as far as possible. In this sense cosmetic products for sun protection have been available for a considerable time and currently represent an economically significant part of the total cosmetic market. Scientific progress which has accompanied the growth in the market has been considerable both in terms of evaluating the efficacy and safety of formulated products according to EU protocols (complementing European cosmetics legislation), and in formulation terms with the availability of safer and more effective sunscreen products.

In general, sunscreens contain a mixture of substances that filter UV rays, such that various radiation ranges can be filtered out to guarantee a wider protection over the entire UV spectrum.

UV sun filters are substances which, when present in cosmetic products for sun protection, are specifically intended for filtering the UV radiation spectrum to protect skin against determined harmful effects of said radiation.

In this field, said UV sun filters are commonly divided into chemical sunscreening agents or physical sunscreening agents, according to their nature and the way they act.

Chemical sunscreening agents are synthetic organic substances which absorb radiation; solar rays excite the filter's molecules to a higher energy state, and are hence absorbed and do not reach the epidermis. The absorbed energy is then released in other forms (thermal energy, vibrational energy). In order to do this, the structure of these substances is particularly complex. Each filter captures and selectively transforms the energy of only certain bands of solar rays, and not the entire solar radiation spectrum. This absorption ensures that the chemical filter "retains" the energy of the sun's rays and transforms the same by various mechanisms into other energy forms.

In contrast, physical sunscreening agents screen all solar rays, are not selective from the molecular viewpoint and form a non-transparent physical barrier which reflects all the light. As there is no energy absorption but only reflection, physical sunscreening agents are particularly preferred from the skin physiology viewpoint as they do not cause overheating of the epidermis.

Physical sunscreening agents are typically opaque mineral substances such as zinc oxide, titanium dioxide, magnesium oxide, iron oxide, and kaolin.

These compounds provide an actual total screening against UV and visible radiation by reflecting and diffusing harmful radiations, due to their opacity, their high intrinsic reflective power, as well as the surface characteristics of the particles.

One of the main disadvantages of physical sunscreening agents, or physical screens, is that they exhibit a "whitening" or "blueing" effect on the skin which is not aesthetically pleasing. In addition, this leads to a tan which is not uniform, indeed "patchy" (depending on whether those areas of skin have or do not have a physical filter, with a greater or lesser extent of physical filter in a determined region) because of particle aggregation phenomena. This disadvantage has been limited, but not resolved, by micronizing the minerals used.

With regard to toxicity to the skin, no restrictions are known for zinc oxide, as being accepted by European legislation without percentage limits, both because it is an insoluble compound and because the zinc ion is an activator of fundamental enzymatic processes and is present in the adult human body at about 1% of body weight. It is however a fairly costly and not very powerful filter. Consequently its use is also greatly limited even for these reasons.

More substantial restrictions have however been proposed for titanium dioxide, which in fact is a non-physiological compound, even though insoluble and used with particles of dimensions very close to nanoparticles. Although widely used, it always remains a catalyst, and under certain circumstances could be activated by solar radiation energy and become a precursor of free radicals. In fact titanium dioxide is a semiconductor, with a band range in the region of 3.0 eV, corresponding to wavelengths of less than about 380 nm. $TiO_2$ is therefore susceptible to excitation by UV rays and once photoexcited it can generate abundant ROS (Reactive Oxygen Species) in aqueous solution [1-3]. Some studies suggest that frequent use of sunscreens containing nanometer sized $TiO_2$ (30-220 nm) can lead to the percutaneous absorption of titanium [4, 5], its penetration into the human strata cornea and in hair follicles [6], as also in cultured fibroblasts [7].

HeLa cells (highly stabilized immortalized tumour cells) die following UV irradiation for 10 minutes if in the presence of $TiO_2$ [5]. Irradiated $TiO_2$ causes oxidative damage to the nucleic acids in cells [7] and breakage of isolated DNA strands [1, 3].

Another material which has been investigated is micronized talc which however has proved to be ineffective even at relatively high percentages (e.g. 25%) without any improvement of the sun protection factor (SPF).

This factor, an indicator of the protective capacity, is expressed by a number denoting how many times the time of exposure to the sun can be multiplied before the skin burns. For example, if the product has a protection factor of 4 it means that one can remain exposed to the sun 4 times longer than that normally envisaged for initial burning (time to erythema) when exposing without protection under the same conditions. It is important to know that the protection factor provides an indication of the filtering action of the product against UVB radiation, but not against UVA radiation, for which other methods exist such as the in vivo PPD (Persistent Pigment Darkening) test or the critical wavelength test (in vitro methods with spectrophotometers).

The need was therefore felt for a sunscreen product of improved screening properties, which at the same time can be perfectly tolerated by the skin, particularly from the viewpoint of its physiology, and able to demonstrate a reduced whitening effect.

The object of the present invention is therefore to provide a product which is able to respond to the aforestated requirements, thus overcoming in this manner the disadvantages of the known art.

SUMMARY

The object indicated above was achieved by a sunscreen product comprising hydroxyapatite or a salt thereof and at least one chemical sunscreening agent, wherein said at least one chemical sunscreening agent and said hydroxyapatite or a salt thereof are in a ratio of 10:1 to 1:3. As will be evident from the following detailed description, hydroxyapatite has surprisingly proved to be an excellent physical sunscreening agent, also in view of its perfect dermal tolerance, and, when synergistically associated with at least one chemical sunscreening agent, surprisingly also acts as a "SPF booster", i.e. is able to enhance the sun protection factor, so advantageously enabling the chemical filter content to be reduced.

Another aspect of the present invention concerns cosmetic compositions preferably in the form of emulsions, comprising said sunscreen product and suitable cosmetic ingredients.

Another aspect of the present invention relates to the use of said cosmetic compositions as sun protection against UV radiation.

BRIEF DESCRIPTION OF THE DRAWINGS

The characteristics and advantages of the present invention will be evident from the following detailed description, from the working examples provided for illustrative and non-limiting purposes and from the appended FIG. 1.

FIG. 1 shows the outcome of the comparison tests between the products obtained according to Examples 1, 2 and 4 respectively, in terms of percentage SPF increase starting from a sunscreen product free of physical filters.

DETAILED DESCRIPTION OF THE INVENTION

The present invention hence relates to a sunscreen product comprising hydroxyapatite or a salt thereof and at least one chemical sunscreening agent, wherein said at least one chemical sunscreening agent and said hydroxyapatite or a salt thereof are in a ratio of 10:1 to 1:3. Hydroxyapatite is a compound already present in the human body, being the main mineral constituent of bone tissue. Indeed, 99% of the calcium in the human body is stored in bone tissue in the form of hydroxyapatite. Hydroxyapatite is a calcium phosphate which in nature constitutes 60-70% of bone and 98% of enamel. Its chemical composition is commonly denoted as $Ca_5(PO_4)_3(OH)$, therefore belonging to the apatite group and containing an $OH^-$ group. The calcium can be present in nature in the said chemical form $Ca_5(PO_4)_3(OH)$, also denoted as $Ca_{10}(PO_4)_6(OH)_2$ to indicate that the elemental cell is formed of two molecules. The $OH^-$ group can be substituted by a fluorine ion ($F^-$), a chlorine ion ($Cl^-$) or carbonate ($CO_3^{2-}$) to form a hydroxyapatite salt. For the purposes of the present invention, the term "hydroxyapatite" also encompasses, in addition to the aforesaid, all polymorphic forms, relative hydrates and solvates, in all ratios between phosphate ions, hydroxyl ions and calcium.

In view of the hydroxyapatite nature itself, it follows a complete dermal and systemic tolerance, differently form zinc oxide and titanium dioxide. It has also been surprisingly found that hydroxyapatite is very highly effective as a physical sunscreening agent for protecting the skin from solar UV rays, this effectiveness being greater than that shown by zinc oxide and titanium dioxide. In addition, a surprisingly reduced whitening effect was noted on the skin after application, though pure hydroxyapatite powder is itself also white. This renders hydroxyapatite a particularly advantageous and convenient compound in the sunscreen product of the invention, as will be evident from the examples provided below.

As aforesaid, in recent years the attention given to the toxicity problems of known sunscreen products, in particular chemical sunscreening agents, has greatly intensified. It has now been surprisingly found that hydroxyapatite is not only an excellent physical sunscreening agent but also acts as an SPF booster, i.e. able to enhance the SPF of a sunscreen formulation, it being hence advantageously possible to reduce the concentration of the chemical sunscreening agents, typically used in known sunscreen products. Thus, the sunscreen product of the invention presents a ratio of chemical sunscreening agent to hydroxyapatite, or a salt thereof, of from 10:1 to 1:3, since above 10:1 it is noted that the chemical filter content would in any event be disadvantageously raised, whereas below 1:3 the content of hydroxyapatite or a salt thereof would render the cosmetic compositions in which the sunscreen product is utilized difficulty distributable and absorbable by the skin.

Preferably, the sunscreen product of the invention further comprises at least one metal selected from the group consisting of zinc, magnesium, manganese, copper, sodium, potassium, lithium, aluminium, silver and bismuth, in the form of a is salt of lactic acid, carbonic acid, acetic acid, $C_3$-$C_{18}$ linear fatty acid, benzoic acid, tartaric acid, citric acid, 3-hydroxypropionic acid, malic acid, succinic acid, mandelic acid, salicylic acid, and mixtures thereof. A synergistic action between hydroxyapatite and said metals has surprisingly been noted, in terms of improved screening effect of solar rays. It has been noted in fact that the presence of said at least one metal improves the screening capability of hydroxyapatite against UV rays. Said metal salts can be co-precipitated with hydroxyapatite or added separately.

More preferably, said at least one metal is selected from the group consisting of zinc, magnesium, manganese, and mixtures thereof, in the form of lactic acid salt, carbonic acid salt and mixtures thereof. It has been noted in fact that in addition to improving the screening capability of hydroxyapatite against UV rays, these metals also improve the dispersion in the cosmetic compositions wherein they are used and their subsequent distribution and absorption on the skin.

According to a preferred embodiment of the invention, the sunscreen product consists of hydroxyapatite, at least one chemical sunscreening agent, and at least one salt selected from the group consisting of Zn lactate, Mg lactate, Mn lactate, Zn carbonate, Mg carbonate, and Mn carbonate. Indeed, in this form the sunscreen product has proved to be particularly compatible with the skin, as well as being extremely stable.

Preferably said at least one chemical filter is selected from derivatives of cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, and mixtures thereof.

More preferably, said at least one chemical filter agent is selected from the group consisting of para-aminobenzoic acid and its salts, N,N,N-trimethyl-4-[(2-keto-3-bornylidene)methyl]aniline methyl sulphate, 2-hydroxybenzoic acid(3,3,5-trimethylcyclohexyl)ester, (2-hydroxy-4-methoxyphenyl)phenyl-methanone, 2-phenylbenzimidazole-5-sulphonic acid and its salts, 3,3'-(1,4-phenylene dimethylene)bis[7,7-dimethyl-2-oxobicyclo[2.2.1]hept-1-yl]methanesulphonic acid and its salts, 1-(4-tert-butylphenyl)-3-(4-methoxyphenyl)-1,3-propanedione, alpha-(2-oxoborn-3-ylidene)toluene-4-sulphonic acid and its salts, 2-cyano-3,3-diphenyl-2-propenoic acid 2-ethylhexyl ester, polymer of N-{(2 and 4)-[2-oxo-born-3-ylidene methyl]benzyl}acrylamide, 2-ethylhexyl 4-methoxycinnamate, ethoxylated 4-aminobenzoic acid, isopentyl 4-methoxycinnamate, 2,4,6-trianiline-(p-carbo-2'-ethylhexyl-1'-oxy)-1,3,5-triazine, drometrizole trisiloxane, benzoic acid 4,4-[[6-[[4-[[(1,1-dimethylethyl)amino]carbonyl]phenyl]amino]-1,3,5-triazine-2,4-diyl]diimino]bis,bis(2-ethylhexyl) ester, 4-methylbenzylidene camphor, 3-benzylidene camphor, 2-ethylhexyl salicylate, 2-ethylhexyl 4-dimethylaminobenzoate, 5-benzoyl-4-hydroxy-2-methoxybenzenesulphonic acid and its salts, 2,2'-methylene-bis-[6-(2H-benzotriazol-2-yl)-4-(1,1,3,3-tetramethylbutyl)]phenol, sodium salt of 2,2'-(1,4-phenylene)bis-1H-benzimidazole-4,6-disulphonic acid, 2,2'-[6-(4-methoxyphenyl)-1,3,5-triazine-2,4-diyl]bis[5-(2-ethylhexyl)oxy]phenyl, dimethicodiethylbenzal malonate, hexyl 2-[4-(diethylamino)-2-hydroxy benzoyl]-benzoate, 2-ethylhexyl 4-(dimethylamino)benzoate, terephthalylidene dicamphor sulphonic acid, methyl 2-aminobenzoate and mixtures thereof.

According to a preferred embodiment, said at least one chemical filter is selected from derivatives of cinnamic acid and its salts, derivatives of salicylic acid and its salts, benzophenones, derivatives of para aminobenzoic acid (PABA) and its salts, dibenzoylmethanes, benzylidenecamphor derivatives, and their mixtures. These compounds have actually shown the greatest synergy with hydroxyapatite, and provide a more marked booster effect. Within this preferred embodiment, the following compounds are further preferred: 2-phenylbenzimidazole-5-sulphonic acid and its salts, 1-(4-tert-butylphenyl)-3-(4-methoxyphenyl)-1,3-propanedione, 2-ethylhexyl 4-methoxycinnamate, 2,4,6-trianiline-(p-carbo-2'-ethylhexyl-1'-oxy)-1,3,5-triazine, 2-ethylhexyl salicylate, hexyl 2-[4-(diethylamino)-2-hydroxy benzoyl]benzoate, and mixtures thereof.

Preferably, in the sunscreen product of the invention, said hydroxyapatite or its salt and said at least one chemical sunscreening agent are in a ratio of 7:1 to 1:2. More preferably, said hydroxyapatite or its salt and said at least one chemical sunscreening agent are in a ratio of 6.5:1 to 1:1.5. It has in fact been noted that an improved booster effect is obtained without increasing the chemical filter content. Preferably, said hydroxyapatite has particle size of 1-200 nm, more preferably 5-95 nm. Said particle size actually allows a better dispersion of the hydroxyapatite in the cosmetic compositions wherein the sunscreen product of the invention is used, thus significantly improving the distribution and absorption thereof on the skin upon application, while at the same time advantageously further reducing the whitening effect.

Another aspect of the present invention relates to cosmetic compositions comprising the sunscreen product as aforedescribed and suitable cosmetic ingredients.

By the term "suitable cosmetic ingredients", it is meant tanning agents, rheological additives, buffering agents, antimicrobial agents, antioxidants, anti-seborrhoea agents, antistatic agents, adsorbents, UV absorbing agents, astringents, chelating agents, hair colouring agents, cosmetic colouring agents, skin conditioners, hair conditioning agents, preserving agents, covering agents, denaturing agents, depigmenting agents, detangling agents, emollients, emulsifying agents, film-forming agents, hair fixing agents, gelling agents, hydrating agents, hydrotropic agents, binding agents, lenitive agents, smoothing agents, opacifiers, oxidizing agents, pearlescent agents, plasticizing agents, propellants, skin protective agents, reducing agents, freshening agents, sebum-restoring agents, solvents, stabilizing agents, emulsion stabilizing agents, toning agents, wetting agents, volumizers and combinations thereof.

It should be understood that all aspects identified as preferred and advantageous for the sunscreen product as aforegiven are also to be considered preferred and advantageous for the cosmetic composition of the present invention.

In said cosmetic composition, the hydroxyapatite is in an amount no higher than 20% by weight on the composition weight. This range ensures a good compromise between high capacity for screening UV rays and minimal whitening effect on the skin.

Preferably, the hydroxyapatite is in an amount of 1 to 15% by weight on the composition weight, more preferably in an amount of 3 to 10% by weight on the composition weight; even more preferably in an amount of 4 to 7% by weight on the composition weight. Said ranges enable a further improvement of the is relationship between high UV ray screening capacity and a minimal whitening effect on the skin, depending on the required SPF level.

According to one embodiment, the composition of the present invention further comprises microfine organic particles, such as methylene bis-benzotriazolyl tetramethylbutylphenol (MBBT) and bis-ethylhexyloxyphenol methoxyphenyl triazine (BEMT). The presence of these microfine organic particles is particularly advantageous as they are able to filter UVA radiation.

The cosmetic composition of the invention can also contain ammonium, triethanolammonium or monoethanolammonium salts, in acetate, lactate, glycolate, gluconate, tartrate or alkylphosphate form, and mixtures thereof.

The cosmetic composition of the invention can be in the form of sun cream, sun gel, sun milk, sun spray, sun emulsion, fluid sun emulsion, sun cream-gel, sun powder, sun lotion, sun protection mask, sun lipo-gel, sun stick, foundation with sunscreen, sun oil, sun paste, products for lightening skin and anti-wrinkle products, all for the face and/or body and/or lips and/or hair.

Preferably the cosmetic composition is in emulsion form.

The milks contain a high percentage of water and are easily spreadable but need to be reapplied more often than the other products. The creams have better adhesiveness and as they are more difficult to spread they are generally used for the face; they are often greasy and for this reason are not indicated for all skin types. Hydrophilic gels are more suited to those with an oily skin because the vehicle in which the sunscreen product is dispersed does not contain oily substances that make skin greasy.

In accordance with a preferred embodiment, said cosmetic composition further comprises at least one eudermic active principle chosen from anti-ageing agents, antioxidants and anti-free radical agents.

Use of the sunscreen product of the invention, as well as of the cosmetic compositions containing the same, hence enables a higher sun filtering power to be achieved than that achievable with known sunscreen products, being at the same time an extremely tolerated product with an advantageously reduced whitening effect upon application to the skin. A further aspect of the present invention thus concerns the use of the aforedescribed cosmetic composition as is sun protection against UV radiation. As will be seen from the examples, these cosmetic compositions comprising the sunscreen product of the invention have proven to be particularly advantageous in filtering solar UV radiation which is known to be harmful as it can cause ageing of the skin, irritations and various types of skin pathologies.

The following working examples of the present invention are provided for illustrative and non-limiting purposes.

EXAMPLES

Example 1

Four compositions were prepared in emulsion form.

The first one was a comparative composition which does not comprise physical sunscreening agents.

The second one was the comparative composition additionally comprising 5% by weight of titanium dioxide.

The third one was the comparative composition additionally comprising 5% by weight of hydroxyapatite.

The fourth one was the above composition, but comprising 5% by weight of hydroxyapatite and additionally comprising Zn, Mg, Mn, lactate.

Said four compositions are given below:

| Composition 1A (comparative) | | |
|---|---|---|
| Ingredients | Function | % by weight |
| PEG-30 dipolyhydroxystearate | emulsifier | 3.00 |
| polyglyceryl-4 diisostearate polyhydroxystearate sebacate | emulsifier | 3.00 |
| ethylhexyl methoxycinnamate | UV filter | 10.00 |
| diethylamino hydroxybenzoyl hexyl benzoate | UVA filter | 10.00 |
| ethylhexyl salicylate | UV filter | 4.00 |
| caprylic/capric triglyceride | emollient | 8.00 |
| $C_{12-15}$ alkyl benzoate | emollient | 8.00 |
| butylene glycol dicaprylate/dicaprate | emollient | 7.00 |
| diisopropyl sebacate | emollient | 4.00 |
| glyceryl behenate/eicosadioate | emollient | 3.00 |
| BHT | antioxidant | 0.05 |
| ethylhexyl triazone | UV filter | 3.00 |
| magnesium stearate | rheological additive | 0.50 |
| butyl methoxydibenzoylmethane | UVA filter | 2.00 |
| glycyrrhetinic acid | skin conditioner | 0.10 |
| extract of calendula officinalis | emollient | 1.00 |
| water | solvent | q.b. |
| glycerin | wetting agent | 0.50 |
| betaine | additive | 0.20 |
| trisodium ethylenediamine disuccinate | chelant | 0.25 |
| allantoin | additive | 0.10 |
| magnesium sulphate | rheological additive | 0.70 |

| Composition 1B (comparative) | | |
|---|---|---|
| Ingredients | Function | % by weight |
| PEG-30 dipolyhydroxystearate | emulsifier | 3.00 |
| polyglyceryl-4 diisostearate polyhydroxystearate sebacate | emulsifier | 3.00 |
| ethylhexyl methoxycinnamate | UV filter | 10.00 |
| diethylamino hydroxybenzoyl hexyl benzoate | UVA filter | 10.00 |
| ethylhexyl salicylate | UV filter | 4.00 |
| caprylic/capric triglyceride | emollient | 8.00 |
| $C_{12-15}$ alkyl benzoate | emollient | 8.00 |
| butylene glycol dicaprylate/dicaprate | emollient | 7.00 |
| diisopropyl sebacate | emollient | 4.00 |
| glyceryl behenate/eicosadioate | emollient | 3.00 |
| BHT | antioxidant | 0.05 |
| ethylhexyl triazone | UV filter | 3.00 |
| magnesium stearate | rheological additive | 0.50 |
| butyl methoxydibenzoylmethane | UVA filter | 2.00 |
| glycyrrhetinic acid | skin conditioner | 0.10 |
| extract of calendula officinalis | emollient | 1.00 |
| water | solvent | q.b. |
| glycerin | wetting agent | 0.50 |
| betaine | additive | 0.20 |
| trisodium ethylenediamine disuccinate | chelant | 0.25 |
| allantoin | additive | 0.10 |
| magnesium sulphate | rheological additive | 0.70 |
| titanium dioxide | | 5.00 |

| Composition 1C | | |
|---|---|---|
| Ingredients | Function | % by weight |
| PEG-30 dipolyhydroxystearate | emulsifier | 3.00 |
| polyglyceryl-4 diisostearate polyhydroxystearate sebacate | emulsifier | 3.00 |
| ethylhexyl methoxycinnamate | UV filter | 10.00 |
| diethylamino hydroxybenzoyl hexyl benzoate | UVA filter | 10.00 |
| ethylhexyl salicylate | UV filter | 4.00 |
| caprylic/capric triglyceride | emollient | 8.00 |
| $C_{12-15}$ alkyl benzoate | emollient | 8.00 |
| butylene glycol dicaprylate/dicaprate | emollient | 7.00 |
| diisopropyl sebacate | emollient | 4.00 |
| glyceryl behenate/eicosadioate | emollient | 3.00 |
| BHT | antioxidant | 0.05 |
| ethylhexyl triazone | UV filter | 3.00 |
| magnesium stearate | rheological additive | 0.50 |
| butyl methoxydibenzoylmethane | UVA filter | 2.00 |
| glycyrrhetinic acid | skin conditioner | 0.10 |
| extract of calendula officinalis | emollient | 1.00 |
| water | solvent | q.b. |
| glycerin | wetting agent | 0.50 |
| betaine | additive | 0.20 |
| trisodium ethylenediamine disuccinate | chelant | 0.25 |
| allantoin | additive | 0.10 |
| magnesium sulphate | rheological additive | 0.70 |
| hydroxyapatite | | 5.00 |

| Composition 1D | | |
|---|---|---|
| Ingredients | Function | % by weight |
| PEG-30 dipolyhydroxystearate | emulsifier | 3.00 |
| polyglyceryl-4 diisostearate polyhydroxystearate sebacate | emulsifier | 3.00 |
| ethylhexyl methoxycinnamate | UV filter | 10.00 |

-continued

Composition 1D

| Ingredients | Function | % by weight |
|---|---|---|
| diethylamino hydroxybenzoyl hexyl benzoate | UVA filter | 10.00 |
| ethylhexyl salicylate | UV filter | 4.00 |
| caprylic/capric triglyceride | emollient | 8.00 |
| $C_{12-15}$ alkyl benzoate | emollient | 8.00 |
| butylene glycol dicaprylate/dicaprate | emollient | 7.00 |
| diisopropyl sebacate | emollient | 4.00 |
| glyceryl behenate/eicosadioate | emollient | 3.00 |
| BHT | antioxidant | 0.05 |
| ethylhexyl triazone | UV filter | 3.00 |
| magnesium stearate | rheological additive | 0.50 |
| butyl methoxydibenzoylmethane | UVA filter | 2.00 |
| glycyrrhetinic acid | skin conditioner | 0.10 |
| extract of *calendula officinalis* | emollient | 1.00 |
| water | solvent | q.b. |
| glycerin | wetting agent | 0.50 |
| betaine | additive | 0.20 |
| trisodium ethylenediamine disuccinate | chelant | 0.25 |
| allantoin | additive | 0.10 |
| magnesium sulphate | rheological additive | 0.70 |
| (Zn, Mg, Mn) hydroxyapatite (lactate) | | 5.00 |

Evaluation of SPF

For all the compositions prepared above, the SPF, i.e. sun protection factor, was evaluated by the COLIPA method (the procedures are described by COLIPA International Sun Protection Factor (SPF) document 001-2003).

As can be seen from FIG. 1, for the first comparative composition the mean SPF was 50, for the second composition with titanium dioxide the mean SPF was 65, whereas for the third composition with the hydroxyapatite according to the invention the mean SPF was surprisingly 65.8 (not shown in FIG. 1). Even more to surprisingly, the fourth composition with (Zn, Mg, Mn) hydroxyapatite (lactate) showed an SPF of 66.2, with a UVA/UVB ratio of 0.33.

Therefore, the compositions 1C and 1D, wherein the ratio between chemical filters and hydroxyapatite was 5.8:1, were shown to be significantly more effective than even the composition comprising the same percentage of titanium dioxide.

Evaluation of Whitening Effect

A panel of 50 people of different ages and having different complexions were asked to apply a sample of composition B onto one arm and a sample of composition C onto the other arm.

The whitening effect of composition C of the invention was noted to be less than that of composition B for everyone; the effect then gradually faded as the skin's hydrolipid film absorbed it.

Moreover, every person demonstrated excellent skin tolerance to the composition of the invention.

Example 2

Four cosmetic products were prepared, specifically a sun milk for the body.

The first milk was a comparative product which does not comprise physical sunscreening agents.

The second one was the comparative milk additionally comprising 4% by weight of titanium dioxide.

The third one was the comparative milk additionally comprising 4% of hydroxyapatite.

The fourth one was the milk as above, but comprising 4% by weight of hydroxyapatite additionally comprising Zn, Mg, Mn lactate.

Said four products are described below:

Body sun milk 2A (comparative)

| Ingredients | Function | % by weight |
|---|---|---|
| PEG-30 dipolyhydroxystearate | emulsifier | 1.500 |
| polyglyceryl-4 diisostearate polyhydroxystearate sebacate | emulsifier | 4.000 |
| ethylhexyl methoxycinnamate | UV filter | 10.000 |
| butyl methoxydibenzoylmethane | UVA filter | 2.000 |
| ethylhexyl salicylate | UV filter | 4.000 |
| caprylic/capric triglyceride | emollient | 8.000 |
| $C_{12-15}$ alkyl benzoate | emollient | 8.000 |
| butylene glycol dicaprylate/dicaprate | emollient | 7.000 |
| diisopropyl sebacate | emollient | 4.000 |
| maize seed oil | emollient | 1.000 |
| glyceryl behenate/eicosadioate | emollient | 2.500 |
| diethylamino hydroxybenzoyl hexyl benzoate | UVA filter | 7.000 |
| ethylhexyl triazone | UV filter | 1.500 |
| magnesium stearate | additive | 0.500 |
| BHT | antioxidant | 0.050 |
| glycyrrhetinic acid | skin conditioner | 0.100 |
| water | solvent | q.b. |
| glycerin | wetting agent | 1.000 |
| betaine | additive | 0.500 |
| allantoin | additive | 0.150 |
| magnesium sulphate | rheological additive | 0.700 |
| xanthan gum | rheological additive | 0.150 |
| trisodium ethylenediamine disuccinate | chelant | 0.300 |
| fragrance | fragrance | 0.300 |

Body sun milk 2B (comparative)

| Ingredients | Function | % by weight |
|---|---|---|
| PEG-30 dipolyhydroxystearate | emulsifier | 1.500 |
| polyglyceryl-4 diisostearate polyhydroxystearate sebacate | emulsifier | 4.000 |
| ethylhexyl methoxycinnamate | UV filter | 10.000 |
| butyl methoxydibenzoylmethane | UVA filter | 2.000 |
| ethylhexyl salicylate | UV filter | 4.000 |
| caprylic/capric triglyceride | emollient | 8.000 |
| $C_{12-15}$ alkyl benzoate | emollient | 8.000 |
| butylene glycol dicaprylate/dicaprate | emollient | 7.000 |
| diisopropyl sebacate | emollient | 4.000 |
| maize seed oil | emollient | 1.000 |
| glyceryl behenate/eicosadioate | emollient | 2.500 |
| diethylamino hydroxybenzoyl hexyl benzoate | UVA filter | 7.000 |
| ethylhexyl triazone | UV filter | 1.500 |
| magnesium stearate | additive | 0.500 |
| BHT | antioxidant | 0.050 |
| glycyrrhetinic acid | skin conditioner | 0.100 |
| water | solvent | q.b. |
| glycerin | wetting agent | 1.000 |
| betaine | additive | 0.500 |
| allantoin | additive | 0.150 |
| magnesium sulphate | rheological additive | 0.700 |
| xanthan gum | rheological additive | 0.150 |
| trisodium ethylenediamine disuccinate | chelant | 0.300 |
| fragrance | fragrance | 0.300 |
| titanium dioxide | | 4.000 |

| Body sun milk 2C | | |
|---|---|---|
| Ingredients | Function | % by weight |
| PEG-30 dipolyhydroxystearate | emulsifier | 1.500 |
| polyglyceryl-4 diisostearate polyhydroxystearate sebacate | emulsifier | 4.000 |
| ethylhexyl methoxycinnamate | UV filter | 10.000 |
| butyl methoxydibenzoylmethane | UVA filter | 2.000 |
| ethylhexyl salicylate | UV filter | 4.000 |
| caprylic/capric triglyceride | emollient | 8.000 |
| $C_{12-15}$ alkyl benzoate | emollient | 8.000 |
| butylene glycol dicaprylate/dicaprate | emollient | 7.000 |
| diisopropyl sebacate | emollient | 4.000 |
| maize seed oil | emollient | 1.000 |
| glyceryl behenate/eicosadioate | emollient | 2.500 |
| diethylamino hydroxybenzoyl hexyl benzoate | UVA filter | 7.000 |
| ethylhexyl triazone | UV filter | 1.500 |
| magnesium stearate | additive | 0.500 |
| BHT | antioxidant | 0.050 |
| glycyrrhetinic acid | skin conditioner | 0.100 |
| water | solvent | q.b. |
| glycerin | wetting agent | 1.000 |
| betaine | additive | 0.500 |
| allantoin | additive | 0.150 |
| magnesium sulphate | rheological additive | 0.700 |
| xanthan gum | rheological additive | 0.150 |
| trisodium ethylenediamine disuccinate | chelant | 0.300 |
| fragrance | fragrance | 0.300 |
| hydroxyapatite | | 4.000 |

| Body sun milk 2D | | |
|---|---|---|
| Ingredients | Function | % by weight |
| PEG-30 dipolyhydroxystearate | emulsifier | 1.500 |
| polyglyceryl-4 diisostearate polyhydroxystearate sebacate | emulsifier | 4.000 |
| ethylhexyl methoxycinnamate | UV filter | 10.000 |
| butyl methoxydibenzoylmethane | UVA filter | 2.000 |
| ethylhexyl salicylate | UV filter | 4.000 |
| caprylic/capric triglyceride | emollient | 8.000 |
| $C_{12-15}$ alkyl benzoate | emollient | 8.000 |
| butylene glycol dicaprylate/dicaprate | emollient | 7.000 |
| diisopropyl sebacate | emollient | 4.000 |
| maize seed oil | emollient | 1.000 |
| glyceryl behenate/eicosadioate | emollient | 2.500 |
| diethylamino hydroxybenzoyl hexyl benzoate | UVA filter | 7.000 |
| ethylhexyl triazone | UV filter | 1.500 |
| magnesium stearate | additive | 0.500 |
| BHT | antioxidant | 0.050 |
| glycyrrhetinic acid | skin conditioner | 0.100 |
| water | solvent | q.b. |
| glycerin | wetting agent | 1.000 |
| betaine | additive | 0.500 |
| allantoin | additive | 0.150 |
| magnesium sulphate | rheological additive | 0.700 |
| xanthan gum | rheological additive | 0.150 |
| trisodium ethylenediamine disuccinate | chelant | 0.300 |
| fragrance | fragrance | 0.300 |
| (Zn, Mg, Mn) hydroxyapatite (lactate) | | 4.000 |

Evaluation of SPF

For all the cosmetic products prepared above, the SPF was evaluated by the COLIPA method (the procedures are described by COLIPA International Sun Protection Factor (SPF) document 001-2003).

As can be seen from FIG. 1, for the first comparative product the mean SPF was 30, for the second product with titanium dioxide the mean SPF was 34.1, whereas for the third product with the hydroxyapatite of the invention the mean SPF was surprisingly 39.5 (not shown in FIG. 1). Even more surprisingly, the to fourth product with (Zn, Mg, Mn) hydroxyapatite (lactate) presented an SPF of 40.3, with a UVA/UVB ratio of 0.35.

Therefore, the products 2C and 2D, wherein the ratio between chemical filters and hydroxyapatite was 6.13:1, were shown to be significantly more effective than even the composition comprising the same percentage of titanium dioxide.

Evaluation of Whitening Effect

A panel of 50 people, different from that of Example 1, of different ages and having different complexions were asked to apply a sample of sun milk B onto one arm and a sample of sun milk C onto the other arm.

The whitening effect of sun milk C of the invention was noted to be less than that of sun milk B for everyone; in this case also, the effect then gradually faded as the skin's hydrolipid film absorbed it.

Moreover, every person demonstrated excellent skin tolerance to the sun milk of the invention.

Example 3

Two sun creams were prepared in the form of emulsions.
The first one was a comparative cream which does not comprise physical sunscreening agents.
The second one was the comparative cream additionally comprising 4.5% by weight of hydroxyapatite.
Said two creams are described below:

| Sun cream 3A (comparative) | | |
|---|---|---|
| Ingredients | Function | % by weight |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |

| Sun cream 3B | | |
|---|---|---|
| Ingredients | Function | % by weight |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |
| hydroxyapatite | | 4.50 |

Evaluation of SPF

For both the sun creams prepared above the SPF was evaluated by the COLIPA method (the procedures are described by COLIPA International Sun Protection Factor (SPF) document 001-2003).

For the comparative cream the mean SPF was 15.3, whereas for the second cream with the hydroxyapatite of the invention the mean SPF was surprisingly 17. Therefore, cream 3B wherein the ratio of chemical filters to hydroxyapatite was 1.4:1 was shown to be significantly more effective than the comparative cream.

Evaluation of Whitening Effect

A panel of 50 people, different from that of the preceding examples, of different ages and having different complexions were asked to apply a sample of sun cream B onto one arm.

A negligible whitening effect for sun cream B of the invention was noted for everyone; in this case also the effect then gradually faded as the skin's hydrolipid film absorbed it.

Moreover, every person showed excellent skin tolerance to the sun cream of the invention.

Example 4

Four sun creams were prepared in emulsion form.

The first one was a comparative cream which does not comprise physical sunscreening agents.

The second one was the comparative cream additionally comprising 6% by weight of titanium dioxide.

The third one was the above sun cream but comprising 6% by weight of hydroxyapatite instead of titanium dioxide.

The fourth one was the above cream, but comprising 6% of hydroxyapatite and additionally comprising Zn, Mg, Mn lactate.

Said four creams are described below:

Sun cream 4A (comparative)

| Ingredients | Function | % by weight |
| --- | --- | --- |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |

Sun cream 4B (comparative)

| Ingredients | Function | % by weight |
| --- | --- | --- |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |
| titanium dioxide | | 6.00 |

Sun cream 4C

| Ingredients | Function | % by weight |
| --- | --- | --- |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |
| hydroxyapatite | | 6.00 |

Sun cream 4D

| Ingredients | Function | % by weight |
| --- | --- | --- |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |
| (Zn, Mg, Mn) hydroxyapatite (lactate) | | 6.00 |

Evaluation of SPF

For all the sun creams prepared above, the SPF was evaluated by the COLIPA method (procedures described by COLIPA International Sun Protection Factor (SPF) document 001-2003).

The SPF of sun cream 4A was 15, whereas as can be seen in FIG. 1, for sun cream with titanium dioxide the mean SPF was 16. Surprisingly cream 4C with hydroxyapatite of the invention presented a mean SPF of 17 (not shown in FIG. 1). Even more surprisingly the fourth cream with (Zn, Mg, Mn) hydroxyapatite (lactate) presented a SPF of 17.5.

Therefore, creams 4C and 4D wherein the ratio of chemical filters to hydroxyapatite was 1.05:1 were shown to be significantly more effective than even the cream comprising the same percentage of titanium dioxide.

Evaluation of Whitening Effect

A panel of 50 people, different from that of the previous examples, of different ages and having different complexions were asked to apply a sample of sun cream B onto one arm and a sample of sun cream C onto the other arm.

The whitening effect of sun cream C of the invention was noted to be less than that of sun cream B for everyone; in this case also the effect then gradually faded as the skin's hydrolipid film absorbed it.

Moreover, every person demonstrated excellent skin tolerance to the sun cream of the invention.

Example 5

Two sun creams were prepared in the form of emulsions.

The first one was a sun cream comprising 15% by weight of titanium dioxide.

The second one was the above sun cream, but comprising 15% by weight of hydroxyapatite instead of titanium dioxide.

Said two creams are described below:

| Sun cream 5A (comparative) | | |
|---|---|---|
| Ingredients | Function | % by weight |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |
| titanium dioxide | UV filter | 15.00 |

| Sun cream 5B | | |
|---|---|---|
| Ingredients | Function | % by weight |
| cetearyl alcohol, PEG-40 castor oil, sodium cetearyl sulphate | emulsifier | 3.15 |
| decyl oleate | emollient | 15.00 |
| octyl methoxycinnamate | UV filter | 3.00 |
| butyl methoxy dibenzoylmethane | UVA filter | 0.50 |
| propylparaben | preservative | 0.10 |
| methylparaben | preservative | 0.30 |
| 2-phenylbenzimidazole-5-sulphonic acid | UV filter | 2.78 |
| sodium hydroxide (10% sol.) | buffer agent | 4.05 |
| disodium EDTA | chelant | 0.10 |
| water | solvent | q.b. |
| xanthan gum | rheological additive | 0.15 |
| hydroxyapatite | UV filter | 15.00 |

Evaluation of SPF

For both the sun creams prepared above the SPF was evaluated by the COLIPA method (the procedures are described by COLIPA International Sun Protection Factor (SPF) document 001-2003).

For the sun cream with titanium dioxide the mean SPF was 24, whereas for the second cream with the hydroxyapatite of the invention the mean SPF was surprisingly 27.

Therefore, cream 5B wherein the ratio of chemical filters to hydroxyapatite was 1:2.4, was shown to be significantly more effective than the cream with titanium dioxide.

Evaluation of Whitening Effect

A panel of 50 people, different from that of the previous Examples, of different ages and having different complexions were asked to apply a sample of sun cream A onto one arm and a sample of sun cream B onto the other arm.

The whitening effect of sun cream B of the invention was noted to be less than that of sun cream A for everyone; in this case also, the effect then gradually faded as the skin's hydrolipid film absorbed it.

Moreover, every person demonstrated excellent skin tolerance to the sun cream of the invention.

From the detailed description and the above reported examples, the advantages achieved by the use of the sunscreen product of the present invention are clear. It has been surprisingly noted that hydroxyapatite not only acts as an excellent physical sunscreening agent with better screening properties than known physical sunscreening agents, particularly $TiO_2$, but also acts as a SPF booster, i.e. able to enhance the SPF of a sunscreen formulation, thus enabling the concentration of chemical sunscreening agents to be reduced.

Moreover, at the same time the sunscreen product proves to be perfectly tolerated by the skin since hydroxyapatite is an element already present in the body, as well as being much more effective than titanium dioxide. In addition, hydroxyapatite shows an extremely low whitening effect, thus overcoming aesthetic drawbacks and problems of proper skin transpiration.

These advantages are particularly appreciated not only in terms of raised perceived and aesthetic pleasantness after application of the cosmetic products containing the filter of the invention, but especially in terms of screening of damaging UV rays, as it proves to be a more than effective aid in preventing skin pathologies.

BIBLIOGRAPHIC REFERENCES

1. Ashikaga T. et al. "Effect of the photocatalytic activity of $TiO_2$ on plasmid DNA" 2000, *Mutation Res*, 466, 1-7
2. Fairhurst D "Surface coating and optimization of microfine oxides in sunscreen formulations. A new technology for sunscreen development", 1997, *Cosmet Toil*, 112, 81-84, 86-88
3. Kobayashi M. et al. "Photocatalytic activity of titanium dioxide and zinc oxide. The effect of organic and inorganic surface treatments", 1997, *Cosmet Toil*, 112, 83-86
4. Tan M. H. et al. "A pilot study on the percutaneous absorption of microfine titanium dioxide from sunscreens", 1996, *Australas J Dermatol*, 37, 185-187
5. Cai R. et al. Photokilling of malignant cells with ultrafine titanium dioxide powder", 1991, *Bull Chem Soc Jpn*, 64, 1268-1273
6. Lademann J. et al. "Penetration of titanium dioxide microparticles in a sunscreen formulation into the horny layer and the follicular orifice", 1999, *Skin Pharmacol Appl Skin Physiol*, 12, 247-256
7. Warner W. G. et al. "Oxidative damage to nucleic acids photosensitized by titanium oxide", 1997, Free Radic Biol Med, 23, 851-858

The invention claimed is:

1. A sunscreen product comprising a mixture of (a) particles consisting of hydroxyapatite or a salt thereof and (b) at least one chemical sunscreening agent, wherein said (b) at least one chemical sunscreening agent and said (a) particles consisting of hydroxyapatite or a salt thereof are in a weight ratio of 10:1 to 1:3.

2. The sunscreen product of claim 1, further comprising (c) at least one metal selected from the group consisting of zinc, magnesium, manganese, copper, sodium, potassium, lithium, aluminum, silver and bismuth, in the form of a salt of lactic acid, carbonic acid, acetic acid, $C_3$-$C_{18}$ linear fatty acid, benzoic acid, tartaric acid, citric acid, 3-hydroxypropionic acid, malic acid, succinic acid, mandelic acid, salicylic acid, and mixtures thereof.

3. The sunscreen product of claim 2, wherein said (c) at least one metal is selected from the group consisting of zinc, magnesium, manganese and mixtures thereof, in the form of a lactic acid salt, a carbonic acid salt, and mixtures thereof.

4. The sunscreen product of claim 1, comprising a mixture of (a) particles consisting of hydroxyapatite, (b) at least one chemical sunscreening agent and (c) at least one salt selected from the group consisting of Zn lactate, Mg lactate, Mn lactate, Zn carbonate, Mg carbonate and Mn carbonate.

5. The sunscreen product of claim 1, wherein said (b) at least one chemical sunscreening agent is selected from derivatives of cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, and mixtures thereof.

6. The sunscreen product of claim 5, wherein said (b) at least one chemical sunscreening agent is selected from the group consisting of para-aminobenzoic acid and its salts, N,N,N-trimethyl-4-[(2-keto-3-bornylidene)methyl]aniline methyl sulphate, 2-hydroxy-benzoic acid (3,3,5-trimethylcyclohexyl)ester, (2-hydroxy-4-methoxyphenyl)phenylmethanone, 2-phenylbenzimidazole-5-sulphonic acid and its salts, 3,3'-(1,4-phenylenedimethylene)bis[7,7-dimethyl-2-oxobicyclo[2.2.1]hept-1-yl]methanesulphonic acid and its salts, 1-(4-tert-butylphenyl)-3-(4-methoxyphenyl)-1,3-propanedione, alpha-(2-oxoborn-3-ylidene)toluene-4-sulphonic acid and its salts, 2-cyano-3,3-diphenyl-2-propenoic acid 2-ethylhexyl ester, polymer of N-{(2 and 4)-[2-oxo-born-3-ylidene methyl]benzyl}acrylamide, 2-ethylhexyl 4-methoxy cinnamate, ethoxylated 4-aminobenzoic acid, isopentyl 4-methoxycinnamate, 2,4,6-trianiline-(p-carbo-2'-ethylhexyl-1'-oxy)-1,3,5-triazine, drometrizole trisiloxane, benzoic acid 4,4-[[6-[[4-[[(1,1-dimethylethyl)amino]carbonyl]phenyl]amino]-1,3,5-triazine-2,4-diyl]diimino]bis,bis(2-ethylhexyl)ester, 4-methyl-benzylidene camphor, 3-benzylidene camphor, 2-ethylhexyl salicylate, 2-ethylhexyl 4-dimethylaminobenzoate, 5-benzoyl-4-hydroxy-2-methoxy-benzenesulphonic acid and its salts, 2,2'-methylene-bis-[6-(2H-benzotriazol-2-yl)-4-(1,1,3,3-tetramethylbutyl)]phenol, sodium salt of 2,2'-(1,4-phenylene)bis-1H-benzimidazole-4,6-disulphonic acid, 2,2'-[6-(4-methoxyphenyl)-1,3,5-triazine-2,4-diyl]bis[5-(2-ethylhexyl)oxy]phenyl, dimethicodiethylbenzal malonate, hexyl 2,[4-(diethylamino)-2-hydroxy benzoyl]-benzoate, 2-ethylhexyl 4-(dimethylamino)benzoate, terephthalylidene dicamphor sulphonic acid, methyl 2-aminobenzoate and mixtures thereof.

7. The sunscreen product of claim 5, wherein said (b) at least one chemical sunscreening agent is selected from derivatives of cinnamic acid and its salts, derivatives of salicylic acid and its salts, benzophenones, derivatives of para aminobenzoic acid (PABA) and its salts, dibenzoylmethanes, benzylidenecamphor derivatives, and mixtures thereof.

8. The sunscreen product of claim 5, wherein said (b) at least one chemical sunscreening agent is selected from the group consisting of 2-phenylbenzimidazole-5-sulphonic acid and its salts, 1-(4-tert-butylphenyl)-3-(4-methoxyphenyl)-1, 3-propanedione, 2-ethyl-hexyl 4-methoxycinnamate, 2,4,6-trianiline-(p-carbo-2'-ethylhexyl-1'-oxy)-1,3,5-triazine, 2-ethylhexyl salicylate, hexyl 2-[4-(diethylamino)-2-hydroxy benzoyl]-benzoate, and mixtures thereof.

9. The sunscreen product of claim 1, wherein said (b) said at least one chemical sunscreening agent and said (a) particles consisting of hydroxyapatite or a salt thereof are in a ratio of 7:1 to 1:2.

10. The sunscreen product of claim 9, wherein said b) said at least one chemical sunscreening agent and said (a) particles consisting of hydroxyapatite or a salt thereof are in a ratio of 6.5:1 to 1:1.5.

11. The sunscreen product of claim 1, wherein said (a) particles consisting of hydroxyapatite have a particle size of 1-200 nm.

12. The sunscreen product of claim 11, wherein said (a) particles consisting of hydroxyapatite have a particle size of 5-96 nm.

13. A cosmetic composition comprising the sunscreen product of claim 1.

14. The cosmetic composition of claim 13, wherein the hydroxyapatite is in an amount not higher than 20% by weight on the composition weight.

15. The cosmetic composition of claim 14, wherein the hydroxyapatite is in an amount of 1 to 15% by weight on the composition weight.

16. The cosmetic composition of claim 15, wherein the hydroxyapatite is in an amount of 3 to 10% by weight on the composition weight.

17. The cosmetic composition of claim 16, wherein the hydroxyapatite is in an amount of 4 to 7% by weight on the composition weight.

18. The cosmetic composition of claim 13,
in the form of a sun cream, sun gel, sun milk, sun spray, sun emulsion, fluid sun emulsion, sun cream-gel, sun powder, sun lotion, sun protection mask, sun lipo-gel, sun stick, foundation with sunscreen, sun oil, sun paste, products for lightening skin, anti-wrinkle products, all for the face and/or body and/or lips and/or hair.

* * * * *